United States Patent [19]

Ayer et al.

[11] Patent Number: 5,246,710
[45] Date of Patent: * Sep. 21, 1993

[54] DOSAGE FORM FOR TREATING CYCLOTHYMIA

[75] Inventors: Atul D. Ayer, Palo Alto; Dana Ridzon, San Francisco, both of Calif.

[73] Assignee: ALZA Corporation, Palo Alto, Calif.

[ * ] Notice: The portion of the term of this patent subsequent to Feb. 9, 2010 has been disclaimed.

[21] Appl. No.: 942,899

[22] Filed: Sep. 10, 1992

Related U.S. Application Data

[63] Continuation-in-part of Ser. No. 842,682, Feb. 27, 1992, Pat. No. 5,185,158.

[51] Int. Cl.$^5$ .............................................. A61K 9/24
[52] U.S. Cl. ....................................... 424/473; 424/468
[58] Field of Search ............................... 424/473, 468

[56] References Cited

U.S. PATENT DOCUMENTS

| | | | |
|---|---|---|---|
| 2,799,241 | 7/1957 | Wurster | 118/24 |
| 2,909,462 | 10/1959 | Warfield et al. | 167/56 |
| 3,845,770 | 11/1974 | Theeuwes et al. | 128/260 |
| 3,916,899 | 11/1975 | Theeuwes et al. | 128/260 |
| 4,016,880 | 4/1977 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,200,098 | 4/1980 | Ayer et al. | 128/260 |
| 4,285,987 | 8/1981 | Ayer et al. | 427/3 |
| 4,327,725 | 5/1982 | Cortese et al. | 128/260 |
| 4,507,303 | 3/1985 | Ishizumi et al. | 514/255 |
| 4,708,868 | 11/1987 | Brickl et al. | 924/80 |
| 4,783,337 | 11/1988 | Wong et al. | 424/468 |
| 4,851,232 | 7/1989 | Urquhart et al. | 424/469 |
| 4,892,778 | 1/1990 | Theeuwes et al. | 428/218 |
| 5,011,841 | 4/1991 | Scappaticci | 514/253 |
| 5,057,321 | 10/1991 | Edgren et al. | 424/413 |
| 5,082,668 | 1/1992 | Wong et al. | 424/473 |
| 5,096,716 | 3/1992 | Deters et al. | 424/473 |

Primary Examiner—Thurman K. Page
Assistant Examiner—D. Gabrielle Phelan
Attorney, Agent, or Firm—Paul L. Sabatine; Edward L. Mandell; Jean M. Duvall

[57] ABSTRACT

A dosage form is provided for administering a drug of the formula

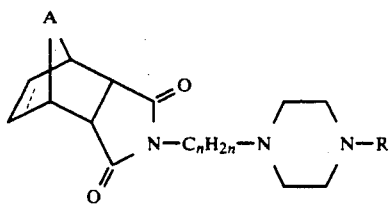

to a patient to produce an anxiolytic benefit in the patient.

1 Claim, 3 Drawing Sheets

DOSAGE FORM FOR TREATING CYCLOTHYMIA

CROSS-REFERENCE TO RELATED APPLICATIONS

This application is a continuation-in-part of U.S. Ser. No. 07/842,682 filed Feb. 27, 1992 now U.S. Pat. No. 5,185,158 issued Feb. 9, 1993. This application is copending with U.S. Ser. No. 07/943,618 filed Sep. 10, 1992. These applications are assigned to the ALZA Corporation of Palo Alto, Calif. and benefit is claimed of their filing date.

FIELD OF THE INVENTION

This invention pertains to a novel and useful dosage form comprising the therapeutic drug represented by the general formula:

The invention concerns also a method for treating depressive disorders by administering the dosage form for delivering the drug of the general formula to a patient in need of antidepressive therapy. The invention relates also to novel compositions comprising the general formula, which compositions are useful for manufacturing the dosage form.

BACKGROUND OF THE INVENTION

A health need exits for a dosage form comprising the therapeutically active drug of the general formula (1):

especially for a dosage form that exhibits an essentially zero order release rate of formula (1) over a long period of time. In formula (1) A is a member selected from the group consisting of an oxygen atom, a methylene group, and an ethylene group; (---) in the six-membered carbocycle ring comprises a member selected from a single bond and a double bond; R is a phenyl group optionally substituted with a member selected from the group consisting of halogen, an alkyl of 1 to 4 carbons, an alkoxy of 1 to 4 carbons, a trifluoromethyl, a 2-pyridyl group and a 2-pyrimidinyl group, and wherein n is an integer of 3 or 4, the base, and the pharmaceutically acceptable salt thereof. The drug can be also in the exo and the endo form thereof.

A presently preferred drug embraced by formula (1) is represented by formula (2).

The drug depicted by formula (2) is known also as tandospirone, or by the name 4,7-methano-1H-isoindole-1,3(2H)-dione, hexahydro-2[4-[-(2-pyrimidinyl)-1-piperazinyl]butyl]-(3aα,4β,7α,7aα)-2-hydroxy-1,2,3-propanetricarboxylate (1:1) or as N-[4-[4-(2-pyrimidinyl)-1-piperazinyl]butyl-2,3-norbornanedicarboximide. The drugs of both formulae are taught in prior art patents U.S. Pat. Nos. 4,507,303; 4,543,355; 4,598,078 and 5,011,841. The beneficial drugs of the formulae are administered by the prior art in rapid release dosage forms, such as tablet, capsule, syrup and suspension. With such rapid release forms, the drug is administered by repeated administration to produce a therapeutic level.

Generally, for rapid release dosage forms, as known to the prior art also as instant release dosage forms, the release rate profile follows the cube root law, that is, the release rate decreases with time, *Inter. J. Pharm.*, Vol. 62, pp 143–151, 1990. This release rate pattern provides unpredictable therapy and it is often accompanied by a period of time, when the patient is not receiving the drug. A critical health need exists for a zero order dosage form that overcomes the shortcomings known to the prior art. A zero order dosage form provides drug continuously to the patient for constant therapy for better health. A dosage form made with zero order drug delivery properties, provides drug at a controlled rate as a zero order plot of the rate of release of drug versus time shows an essentially straight line that indicates the rate of release is independent of time. A dosage form, according to the present invention, that provides for the zero order administration of drugs of formulae of (1) and (2), would represent a major advancement of the drug delivery art, because the controlled and sustained zero order release of drug in a known and uniform dose over a long period of time reinforces better therapy.

In light of the above presentation, it will be evident to those versed in the dispensing art, that a pressing need exists for a dosage form possessing a zero order rate of release that can deliver the valuable drug of formulae 1 and 2 for its therapy. The pressing need exists for a dosage form having a zero order rate of release, which zero order is generated by osmotic activity, while simultaneously maintaining the physical and chemical integrity of the osmotic dosage form during the drug delivery period.

OBJECTS OF THE INVENTION

Accordingly, in view of the above presentation, it is an immediate object of this invention to provide a dosage form for delivering, at an essentially zero order rate of release, the drug of formulae (1) and (2) to a patient in need of formulae (1) and (2) drug therapy.

Another object of the present invention is to provide a zero order dosage form hat substantially overcomes the deficiencies associated with the prior art.

Another object of the present invention is to provide a dosage form for administering formulae (1) and (2)

drug at a zero order rate of release dose over a prolonged period of time for treating depressive disorders.

Another object of the present invention is to provide a dosage form that makes available zero order sustained and controlled formula (2) tandospirone therapeutic activity for anxiolytic therapy.

Another object of the invention is to provide a novel dosage form manufactured as an osmotic dosage form that can administer a drug embraced by formula (1) comprising tandospirone at a zero order rate to a biological receptor site to produce the desired formula (1) comprising tandospirone pharmaceutical effects.

Another object of the present invention is to provide a dosage form manufactured as an osmotic dosage form that substantially reduces and/or substantially eliminates the unwanted influences of the gastrointestinal environment of use and still provides controlled administration of formulae (1) and (2) as exemplified by tandospirone over time.

Another object of the present invention is to provide an osmotic operated dosage form that maintains its physical and chemical integrity while producing an internal high osmotic pressure during the delivery of tandospirone.

Another object of the present invention is to provide a dosage form adapted for oral administration of tandospirone, which dosage form comprises a first tandospirone composition and a second push composition that act together for the rate controlled administration to a patient over time.

Another object of the present invention is to provide a composition of matter comprising tandospirone, which composition is useful for manufacturing a dosage form.

Another object of the present invention is to provide a complete pharmaceutical regimen comprising a composition comprising tandospirone that can be dispensed from an osmotic delivery device, the use of which requires intervention only initiation and possibly for the termination of the regimen.

Another object of the invention is to provide a method for treating depressive disorder comprising administering an antidepressive effective dose of tandospirone from a zero order dosage form, to a warm-blooded animal.

Another object of the present invention is to provide the use of a dosage form for administering tandospirone from a dosage form at an osmotically powered rate over time, wherein the tandospirone is selected from the group consisting of a base, a salt, an endo and an exo form.

Other objects, features and advantages of the invention will be more apparent to those versed in the dispensing arts, from the following detailed specification, taken in conjunction with the drawings and the accompanying claims.

BRIEF DESCRIPTION OF THE DRAWINGS

In these drawing figures, which are not drawn to scale, but are set forth to illustrate various embodiments of the invention the drawing figures are as follows.

Drawing

Drawing

Drawing

Drawing

In the drawing figures and in the specification like parts in related drawing figure are identified by like numbers. The terms appearing earlier in the specification and in the description of the drawings, as well as embodiments thereof, are further described elsewhere in the disclosure.

DETAILED DESCRIPTION OF THE DRAWING FIGURES

Figure 1:
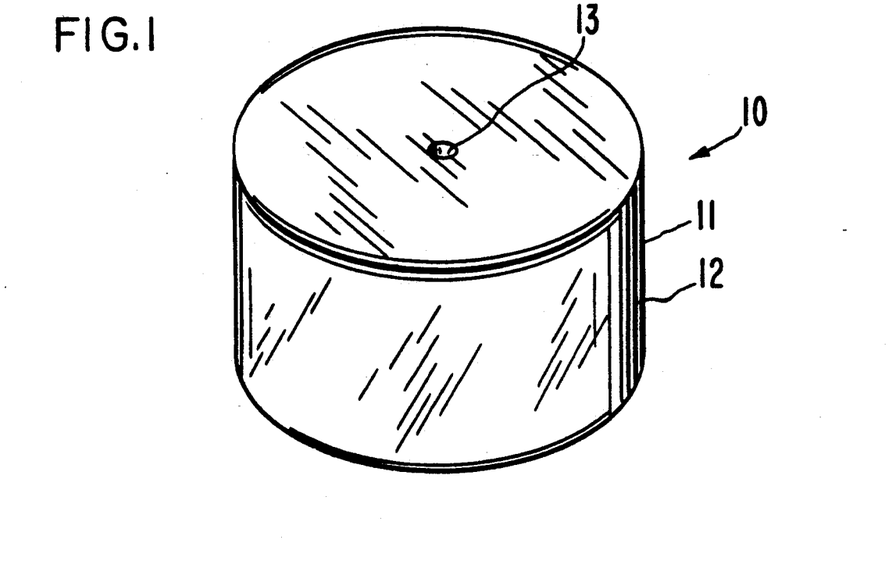
FIG. 1 is a view of a dosage form designed and shaped for administering orally the drugs of formulae (1) and (2) including presently preferred tandospirone to biological, gastrointestinal receptors of drugs of formulae (1) and (2) including tandospirone.

Turning now to the drawing figures in detail, which drawing figures are an example of the dosage forms provided by this invention, and which example is not to be construed as limiting the invention, one example of the dosage form is illustrated in drawing FIG. 1 and designated by the numeral 10. In drawing FIG. 1, dosage form 10 comprises a body member 11 comprising a wall 12 that surrounds and encloses an internal compartment, not seen in drawing FIG. 1. Wall 12 keeps its physical integrity and structure in the presence of osmotic and hydrodynamic pressure generated within dosage form 10 during operation of dosage form 10. Dosage form 10 comprises at least one exit means 13 for connecting the interior of dosage form 10 with the exterior environment of use.

Figure 2:
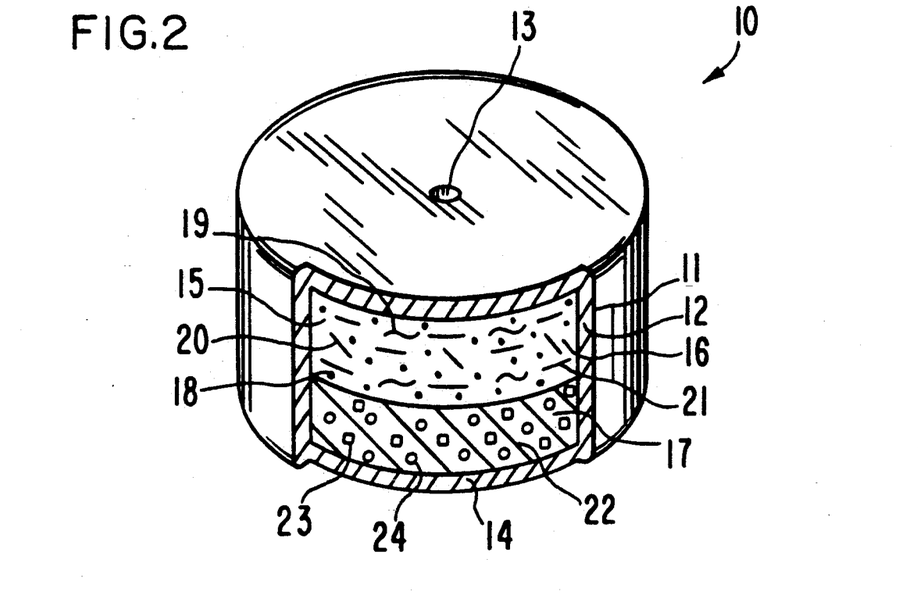
FIG. 2 is an opened-view of the dosage form of drawing FIG. 1, for illustrating the total structure of the dosage form.

In drawing FIG. 2, dosage form 10, manufactured as an osmotic dosage form, is seen in opened view. In drawing FIG. 2, dosage form 10 comprises body 11, wall 12 that is sectioned at 14, depicts wall 12 that surrounds and defines an internal compartment 15. Wall 12 comprises at least one exit means 13 that connects compartment 15 with the exterior of dosage form 10. Dosage form 10 can comprise more than one exit means 13.

Wall 12 of dosage form 10 comprises a composition that is permeable to the passage of an exterior fluid present in the fluid environment of use, and the wall-forming composition is substantially impermeable to the drug of formulae (1) and (2), and to other components present in compartment 15. The composition is semipermeable, it is nontoxic and substantially inert. The composition maintains its physical and chemical integrity, that is, it does not change its chemical nature, independently of the structure of wall 12. Wall 12 comprises from 70 weight percent, (wt %), to 100 wt % of a cellulose wall-forming polymer. The polymer comprises a member selected from the group consisting of cellulose acylate, cellulose diacylate, cellulose triacylate, cellulose acetate, cellulose diacetate and cellulose triacetate. In another operative manufacture, wall 12 comprises additionally from 0 wt % to 25 wt % of a cellulose ether selected from the group consisting of hydroxypropylcellulose and hydroxypropylmethylcellulose; and from 0 wt % to 15 wt % of a polyethylene glycol. The total weight percent of all components comprising wall 12 is equal to 100 wt %.

Dosage form 10, as seen in drawing FIG. 2, in compartment 15 comprises a drug layer 16 and a push layer 17. Drug layer 16 and push layer 17 act together, during operation of dosage form 10, for the delivery of drug of formulae (1) and (2), as exemplified by tandospirone, to a patient in need of formulae (1) and (2) therapy. Drug layer 16 and push layer 17 also act with wall 12 for the controlled rate of release of drug of formulae (1) and (2) over time.

Drug layer 16 comprises 5 wt % to 80 wt % of a drug selected from formula (1) as exemplified by formula (2) which depicts tandospirone, and its therapeutically acceptable salts, identified by dots 18. The therapeutic dose of a formula (1) drug as represented by tandospirone 18 in a single dosage form 10, expressed in milligrams, (mg), is from 1 mg to 750 mg. Individual dosage form 10 comprises 2, 5, 10, 40, 50, 80, 120, 160, 250, 300, 500 and 750 mg of drug for administering in a single dose, or in more than one dose. The pharmaceutically acceptable non-toxic salts useful for the present purpose comprise a member selected from the group consisting of inorganic, organic, hydrochloric, hydrobromic, sulfuric, phosphoric, acetic, propionic, butyric, tartaric, citric, maleic, fumaric, lysine, succinic, palmitic, and glycine salts.

Drug layer 16 comprises additionally a polymer 19, depicted by a wavy line, for transporting drug 18 from dosage form 10. Polymer 19, in one manufacture comprises the structure $(-O-CH_2CH_2-)_n$ wherein n is a positive whole number of 4500 to 5000. Representation of the polymer 19 is a poly(oxyethylene) of approximate average molecular weight of $2 \times 10^5$. Drug layer 16, comprises in another manufacture a polymer composition comprising a first polymer and a second polymer blended together to function as a unit polymer 19 comprising drug 18. The first polymer comprises the polymer described immediately above of the structure $-(O-CH_2CH_2-)_n$, wherein n is a whole number of 6500 to 7500 as represented by poly(oxyethylene) of the approximate average molecular weight of $3 \times 10^5$. In the polymer composition, the concentration of the first polymer is 20 to 50 wt % and the composition of the second polymer is 2 to 40 wt %, with the proviso that, when the concentration of the second polymer exceeds 9 wt %, that is, from 9 to 40 wt %, dosage form 10 is manufactured with at least two exits to prevent bursting of dosage form 10. The concentration of the first and second polymer, when presented together in dosage form 10, is 35 to 80 wt %. Polymer 19, present as a single polymer, or as a first and second polymer a pair, effectively transports, in both manufacture, drug 18 from dosage form 10, and they release drug 18 of formulae (1) and (2) to a drug receptor for its therapy. It is unexpected polymer 19, in both manufactures, can perform its housing-transporting-releasing-compositional functions as a complex drug composition comprising the drug of formulae (1) and (2) essentially-free of any bonding of drug 18 to polymer 19. Drug layer 16 comprises optionally from zero wt % to 3 wt % of a lubricant 20 such as magnesium stearate or calcium stearate; from 0 to 20 wt % of an osmotically active compound 21 such as a member selected from the group consisting of an inorganic salt, an organic salt, a compound containing an amino group, a carbohydrate, an acid and an ester; and 0 wt % to 4 wt % of an anti-oxidant for imparting stability to the drug composition 16, said anti-oxidant comprising a member selected from the group consisting of ascorbic acid, 2,3-butyl hydroxyanisole, mono-tertiary butyl hydroquinone, and butylated hydroxytoluene; and 0 to 10 wt % of a drug-powder coating agent poly(vinylpyrrolidone) having a 3,000 to 1,250,000 molecular weight. The total weight percent of all components in drug 16 is equal to 100 wt %.

Second layer 17 comprises 50 wt % to 75 wt % of a polymer 22 comprising the repeating molecular unit $-(-O-CH_2CH_2-)-_n$, wherein n is a positive whole number of 90,000 to 230,000. Representative of polymer 22 embraced by the repeating molecular unit is a poly(alkaline oxide) comprising poly(ethylene oxide) comprising an approximate average molecular weight of $4 \times 10^6$ to $10 \times 10^6$. Polymer 22 provides unexpected operating advantages as the polymer maintains its chemical composition during operation as it imbibes an external aqueous fluid including biological fluid while simultaneously pushing drug layer 16 from dosage form 10 essentially-free of substantially mixing with drug layer 16. Second layer 17 comprises also 15 wt % to 35 wt % of an osmotically active compound 23, represented by small squares. Representation of osmotically effective compounds comprises salts, esters, carbohydrates and acids, such as a member selected from the group consisting of magnesium sulfate, magnesium chloride, sodium chloride, lithium chloride, potassium sulfate, sodium sulfate, lithium sulfate, potassium chloride, ammonium chloride, potassium lactate, mannitol, urea, inositol, magnesium succinate, tartaric acid, raffinose, sorbitol, sucrose, fructose, glycose and the like. Second layer 17 comprises also 0.1 wt % to 20 wt % of a cellulose ether 24 represented by small circles. Representative of cellulose ethers comprise a member selected from the group consisting of hydroxypropylcellulose and hydroxypropylmethylcellulose having a molecular weight of 9,000 to 22,500. The composition comprises 0 wt % to 5 wt % of a lubricant such as stearic acid, magnesium stearate, calcium stearate, calcium oleate, oleic acid and caprylic acid. The polymers disclosed herein are commercially available from the Union Carbide Corporation, South Charleston, W. Va.

The expression, "exit means 13", as used herein, comprises means and methods suitable for the metered release of the therapeutic drug 18 from compartment 15 of dosage form 10. The exit means 13 comprises at least one passageway, orifice, bore, aperture, pore, porous element, hollow fiber, capillary tube, porous overlay, and porous element that provides for the osmotic controlled release of drug 17. The expression exit means 13 includes a material that erodes or is leached from wall 12 in a fluid environment of use to produce at least one osmotic dimensioned passageway 13 is dosage form 10. Representative materials suitable for forming a passageway, or a multiplicity of passageways comprise a leachable poly(glycolic) acid or poly(lactic) acid polymer in wall 12, a gelatinous filament, poly(vinyl alcohol), leachable polysaccharides, salts and oxides. A pore passageway, or more than one pore passageways can be formed by leaching a leachable compound, such as sorbitol, from wall 12. The passageway possessing controlled release dimensions such as round, triangular, square, elliptical, and the like, for the metered release of drug 17 from dosage form 10. Dosage form 10 can be construed with one or more passageways in spaced apart relationship on a single surface or on more than one surface of dosage form 10. Passageways and equipments for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

DESCRIPTION OF PROCESSES FOR MANUFACTURING THE DOSAGE FORM OF THE INVENTION

Wall 12 of osmotic dosage form 10 can be formed in one technique using the air suspension procedure. This procedure consists in suspending and tumbling the compressed layers in a current of air and wall forming composition until a wall is applied to the drug forming compartment. The air suspensions procedure is well-suited for independently forming the a wall. The air suspension procedure is described in U.S. Pat. No. 2,799,241: *J. Am. Pharm. Assoc.*, Vol. 48, pages 451 to 459, 1959; and ibid. Vol. 49, pages 82 to 84, 1960. Osmotic dosage forms can also be coated with a wall-forming composition in a Wurster ® air suspension coater, using acetone-water cosolvent, 90:10, wt:wt, using 2.5 to 7 wt % polymer solids. The Aeromatic ® air suspension coater using a methylene dichloride methanol cosolvent, 87:13, v:v, also can be used for applying the wall. Other wall forming techniques, such as pan coating, can be used for providing the dosage form. In the pan coating system, wall forming compositions are deposited by successive spraying of the composition on the bilayered compartment, accompanying by tumbling in a rotating pan. A larger volume of cosolvent can be used to reduce the concentration of polymer solids to produce a thinner wall. Finally, the wall coated compartments are laser or mechanically drilled and dried in a forced air oven at 30° C. to 50° C. for a week to free the dosage form of solvent. Generally, the walls formed by these techniques have a thickness of 2 to 20 mils (0.051 to 0.51 mm) with a presently preferred thickness of 2 to 6 mils (0.051 to 0.15 mm).

Dosage form 10 of the invention is manufactured by standard manufacturing techniques. For example, in one manufacture, the beneficial drug and other ingredients comprising the first layer facing the exit means are blended and pressed into a solid layer. The drug and other ingredients can be blended also with a solvent and mixed into a solid or semisolid formed by conventional methods such as ball-milling, calendering, stirring or rollmilling and then pressed into a preselected shape. The layer possesses dimensions that correspond to the internal dimensions of the area the layer is to occupy in the dosage form and it also possesses dimensions corresponding to the second layer for forming a contacting arrangement therewith. Next, the osmopolymer layer is placed in contact with the drug layer. The layering of the drug layer and the osmopolymer layer can be fabricated by conventional press-layering techniques. Finally, the two layer compartment forming members are surrounded and coated with an outer wall. A passageway is laser drilled through the wall to contact the drug layer, with the dosage form optically oriented automatically by the laser equipment for forming the passageway on the preselected surface.

In another manufacture, dosage form 10 is manufactured by the wet granulation technique. In the wet granulation technique, the drug and the ingredients comprising the first layer are blended using an organic or inorganic solvent, such as isopropyl alcohol-methylene dichloride 80/20 v/v as the granulation fluid. Other granulating fluid, such as water or denatured alcohol 100%, can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. the blend is dried for 18 to 24 hours at 25° C. to 40° C. The dry granules are screened then with a 16 mesh screen. Next, a lubricant is passed through an 60 mesh screen and added to the dry screened granule blend. The granulation is put into milling jars and mixed on a jar mill for 2 to 10 minutes. The first and second layer compositions are pressed into a layered tablet, for example, in a Manesty ® layer press.

Another manufacturing process that can be used for providing the compartment-forming composition comprises blending the powdered ingredients in a fluid bed granulator. After the powdered ingredients are dry blended in the granulator, a granulating fluid, for example poly(vinyl-pyrrolidone) in water, is sprayed onto the powders. The coated powders are then dried in a granulator. This process coats-agglomerates all the ingredients present therein while spraying the granulating fluid. After the granules are dried, a lubricant such as stearic acid or magnesium stearate is blended as above into the mixture. The granules are pressed then in the manner described above.

The osmotic device of this invention is manufactured in another embodiment by mixing a drug with composition forming ingredients and pressing the composition into a solid layer possessing dimensions that correspond to the internal dimensions that correspond to the internal dimensions of the compartment space adjacent to a passageway. In another embodiment, the drug and other first composition forming ingredients and a solvent are mixed into a solid, or a semi-solid, by conventional methods such as ballmilling, calendering, stirring or rollmilling, and then pressed into a preselected layer forming shape.

In the manufactures as presented above, the manufacture comprising a layer of a composition comprising an osmopolymer and an optional osmagent are placed in contact with the layer comprising the drug, and the two lamina comprising the layers are surrounded with a semipermeable wall. The layering of the first drug composition and the second osmopolymer optional osmagent composition can be accomplished by using a conventional two-layer tablet press technique. The wall can be applied by molding, spraying or dipping the pressed shapes into IO wall forming materials. Another and presently preferred technique that can be used for applying the wall is the air suspension coating procedure. This procedure consists in suspending and tumbling the two layers in a current of air until the wall forming composition surrounds the layers. The air suspension procedure is described in U.S. Pat. No. 2,799,241; *J. Am. Pharm. Assoc.*, Vol. 48, pp 451–459 (1979); and, ibid, Vol. 49, pp 82–84 (1960). Other standard manufacturing procedures are described in *Modern Plastics Encyclopedia*, Vol 46, pp 62–70 (1969); and in *Pharmaceutical Science*, by Remington, 14th Ed., pp 1626–1979, (1970), published by Mack Publishing Co., Easton, Pa. The dosage forms can be manufactured by following the teaching in U.S. Pat. Nos. 4,327,725; 4,612,008; 4,783,337; 4,863,456; and 4,902,514.

Exemplary solvents suitable for manufacturing the wall, the laminates and laminae include inert inorganic and organic solvents that do not adversely harm the materials and the final wall of the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol,isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethylacetate, methylene dichloride, ethylene dichloride, propylene dichloride, carbon chloroform, a nitroethane, nitropropane, tetrachloroethane, ethyl ether, isopropyl ether, cyclohexane, cycl-octane, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES PROVIDED BY THE INVENTION

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

A dosage form adapted, designed and shaped a an osmotic drug delivery device is manufactured as follows: first, 12.5 kg of micronized tandospirone, 11.25 kg of poly(ethylene oxide) possessing a 200,000 molecular weight are added to a Freund Flo-Coater's ® bowl, a fluid bed granulator. The bowl was attached to the coater and granulation process was initiated for effecting granulation. Next, the dry powders were air suspended and mixed for 7 minutes. Then, a solution prepared by dissolving 1000 g of poly(vinylpyrrolidone) identified as K29-32 having an average molecular weight of 40,000, in 15,667 g of water was sprayed from 3 nozzles onto the powder. The coating conditions were monitored during the process of aqueous poly(vinylpyrrolidone) as follows: solution spray rate of 125 g/min from each nozzle for a total spray rate of 375 g/min; inlet temperature 45° C.; and process air flow of 1000 cfm.

The coating process was computerized and automated in cycles. Each cycle contained 30 seconds of solution spraying followed by two seconds of drying and 10 seconds of filter bags shaking to unglue and possible powder deposits. At the end of the solution spraying, 16,667 g, the coated granulated particles were continued with the drying process for 25 minutes. The machine was turned off, and the coated granules were removed from the Flo-Coater. The coated granules were sized using a Fluid Air Mill. The granulation was transferred to a Rotocone ®, mixed and lubricated with 250 g of magnesium stearate and mixed with 12.5 g of butylated hydroxytoluene.

Next, a push composition is prepared as follows: first, 415.5 g of pharmaceutically acceptable poly(ethylene oxide) comprising a 7,500,000 molecular weight, 150 g of sodium chloride and 6 g of ferric oxide separately are screened through a 40 mesh screen. Then, all the screened ingredients are mixed with 30 g of hydroxypropylmethylcellulose comprising a 11,200 molecular weight to produce a homogeneous blend. Next, 300 mg of denatured anhydrous alcohol is added slowly to the blend with continuous mixing for 5 minutes. The freshly prepared wet granulation is passed through a 20 mesh screen, allowed to dry at room temperature for 16 hours, and again passed through a 20 mesh screen. The screened granulation is mixed with 1.5 of magnesium stearate in a rollermill for 5 minutes.

Next, the tandospirone drug composition and the push composition are compressed into bilayered tablets. First, 352 mg of the tandospirone composition is added to a punch and tamped, then, 175 mg of the push composition is added and the layers are pressed under a pressure head of two tons into a 7/16" (1.11 cm) diameter contacting layered arrangement.

The bilayered arrangements are coated with a semi-permeable wall. The wall forming composition comprises 95% cellulose acetate having a 39.8% acetyl content, and 5% polyethylene glycol having a molecular weight of 3350. The wall-forming composition is dissolved in an acetone:water (90:10 wt:wt) cosolvent to make a 4% solids solution. The wall forming composition is sprayed onto and around the bilayers in a 24" Vector Hi-Coater.

Figure 3A:
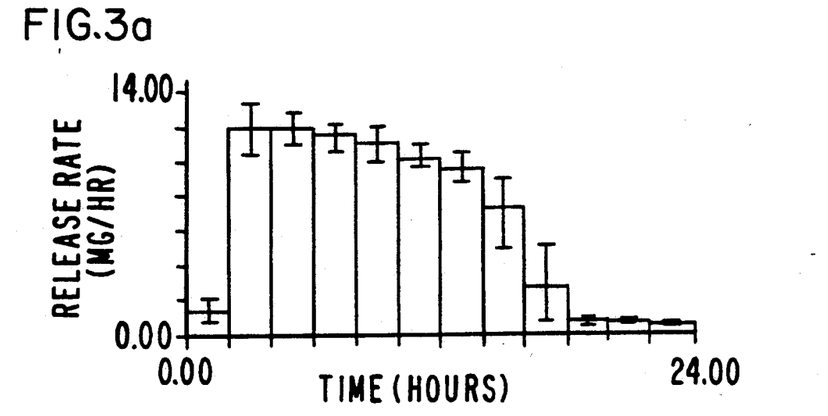
FIG. 3a and 3b are graphs that depict the dose of tandospirone released per hour over a prolonged period of twenty-four hours and the cumulative dose released from the dosage form.
Figure 3B:
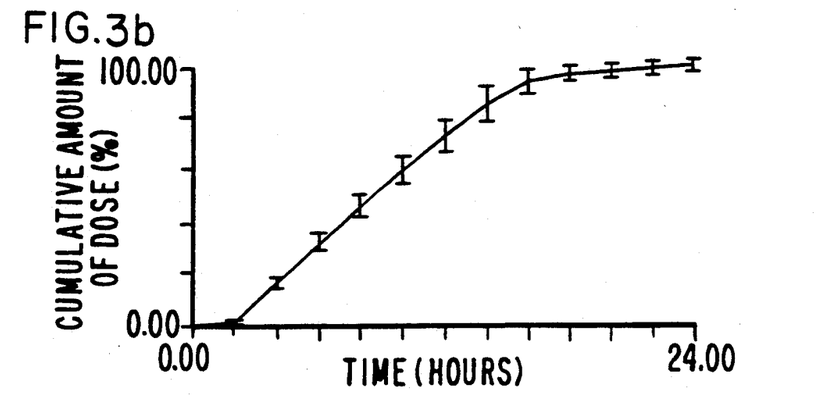

Next, two 25 mil (0.635 mm) exit passageways are mechanically drilled through the semipermeable wall to connect the drug layer with the exterior of the dosage system. The residual solvent is removed by drying for 48 hours at 50° C. and 50% humidity. Next, the osmotic systems are dried for 1 hour at 50° C. to remove excess moisture. The dosage form produced by this manufacture provides 50 wt % tandospirone, 45 wt % poly(ethylene oxide) possessing a 200,000 molecular weight, 4 wt % poly(vinyl pyrrolidone) possessing a 40,000 molecular weight, 0.95 wt % magnesium stearate, and 0.5 wt % butyl hydroxytoluene. The push composition comprises 68.8 wt % poly(ethylene oxide) comprising a 7,500,000 molecular weight, 25 wt % sodium chloride, 5 wt % hydroxypropylmethylcellulose possessing 11,200 molecular weight, 1.0 wt % ferric oxide and 0.2 wt % magnesium stearate. The semipermeable wall comprises 95 wt % cellulose acetate comprising a 39.8% acetyl content, and 5.0 wt % polyethylene glycol comprising a 3350 molecular weight. The dosage form comprises two passageways, 25 mils (0.635 mm), and it had a tandospirone mean release rate of 11.67 mg/hr. Accompanying FIGS. 3a and 3b depict the delivery pattern for a dosage form provided by this example.

EXAMPLE 2

Figure 4:
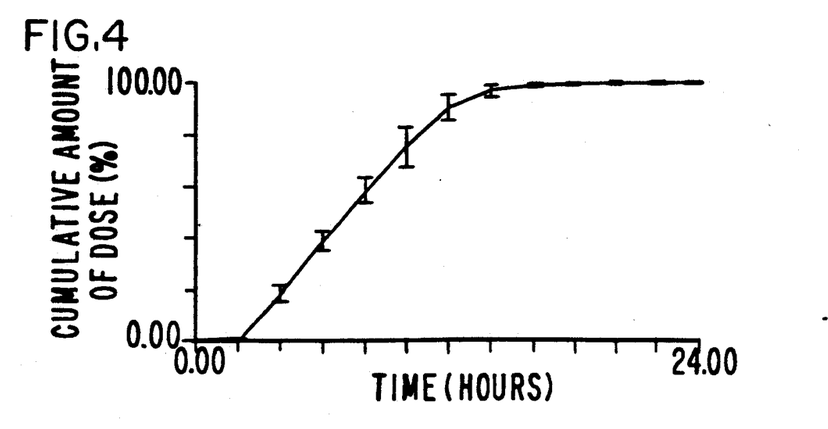
FIG. 4 is a graph depicting the cumulative amount of tandospirone released at a controlled rate from a different dosage form provided by the invention; and, Drawing

Following the procedure of Example 1, an osmotic dosage form comprising a drug dose of 80 mg of drug was prepared to provide the following dosage form: a drug layer comprising 50 wt % of tandospirone, 25 wt % of poly(ethylene oxide) comprising a 200,000 molecular weight, 19.95 wt % of poly(ethylene oxide) comprising a 300,000 molecular weight, 4.0 wt % of poly(vinyl pyrrolidone), 0.05 wt % of butyl hydroxytoluene, and 1.0 wt % magnesium stearate. The push composition comprises 68.75 wt % poly(ethylene oxide) of 7,500,000 molecular weight, 25.0 wt % sodium chloride, 5.0 wt % hydroxypropylmethylcellulose, 1 wt % ferric oxide and 0.25 wt % magnesium stearate. The wall comprises 95 wt % cellulose acetate comprising 39.8% acetyl content and 5 wt % poly(ethylene glycol) of 3350 molecular weight. The dosage form comprises two 30 mils orifices, 0.762 m, and the cumulative release rate is depicted in FIG. 4. In this example, the drug layer weighed 176 mg, consisting of a dose or 80 mg of tandospirone and a tandospirone overage of 8 mg.

EXAMPLE 3

The procedures of Example 1 and Example 2 are followed in this example to provide a dosage form comprising a total drug content of 132 mg of tandospirone, a tandospirone does of 120 mg, and a mean release rate of 9.17 mg/hr of tandospirone over a 15.6 hour period of time. In this example, the total weight of the drug layer was 264 mg, the total weight of the push layer was 130 mg, the dosage form had a diameter of 13/32 inches (10.32 mm) and 2 orifices of 30 mils (0.762 mm).

EXAMPLE 4

A dosage form is provided comprising the following: a total tandospirone of 88 mg; a drug dose of tandospirone of 80 mg; a drug layer comprising 50 wt % tandospirone, 70 wt % poly(ethylene oxid) comprising a 200,000 molecular weight, 4 wt % poly(vinyl pyrrolidone) of 40,000 molecular weight, 0.95 wt % magnesium stearate, and 0.05 wt % butyl hydroxytoluene; the push layer weighed 174 mg and comprises 68.75 wt % poly(ethylene oxide) of 7,500,000 molecular weight, 25 wt % sodium chloride, 6 wt % hydroxypropylmethylcellulose, 1 wt % ferric oxide, and a 0.25 wt % magnesium stearate; a wall comprising 95 wt % cellulose acetate comprising an acetyl content of 39.8%, and 5 wt % polyethylene glycol. The dosage form comprises two 25 mils (0.635 mm) passageways, and a nominal $T_{90}$ over 14 hours means release rate of 6.1 mg/hr of tandospirone.

EXAMPLES 5 AND 6

Two dosage forms comprising a total dose of 176 mg of tandospirone were prepared wherein both dosage forms comprised a 352 mg drug layer comprising 50 wt % tandospirone, 33.75 wt % of poly(ethylene oxide) comprising a 200,000 molecular weight, 11.25 wt % of poly(ethylene oxide) comprising a 300,000 molecular weight, 4 wt % of poly(vinyl pyrrolidone) comprising 40,000 molecular weight, and 1 wt % magnesium stearate. The push layer was as described in Example 4. One dosage form provided by this example comprises one passageway of 25 mils diameter (0.635 mm) and a nominal $T_{90}$, mean release rate of 10.820 mg/hr for 15.7 hours; and the other dosage form comprises two passageways of 25 mils diameter (0.635 mm), a nominal $T_{90}$, and a mean release rate of 11.128 mg/hr for 15 hours.

EXAMPLES 7 AND 8

Figure 5:
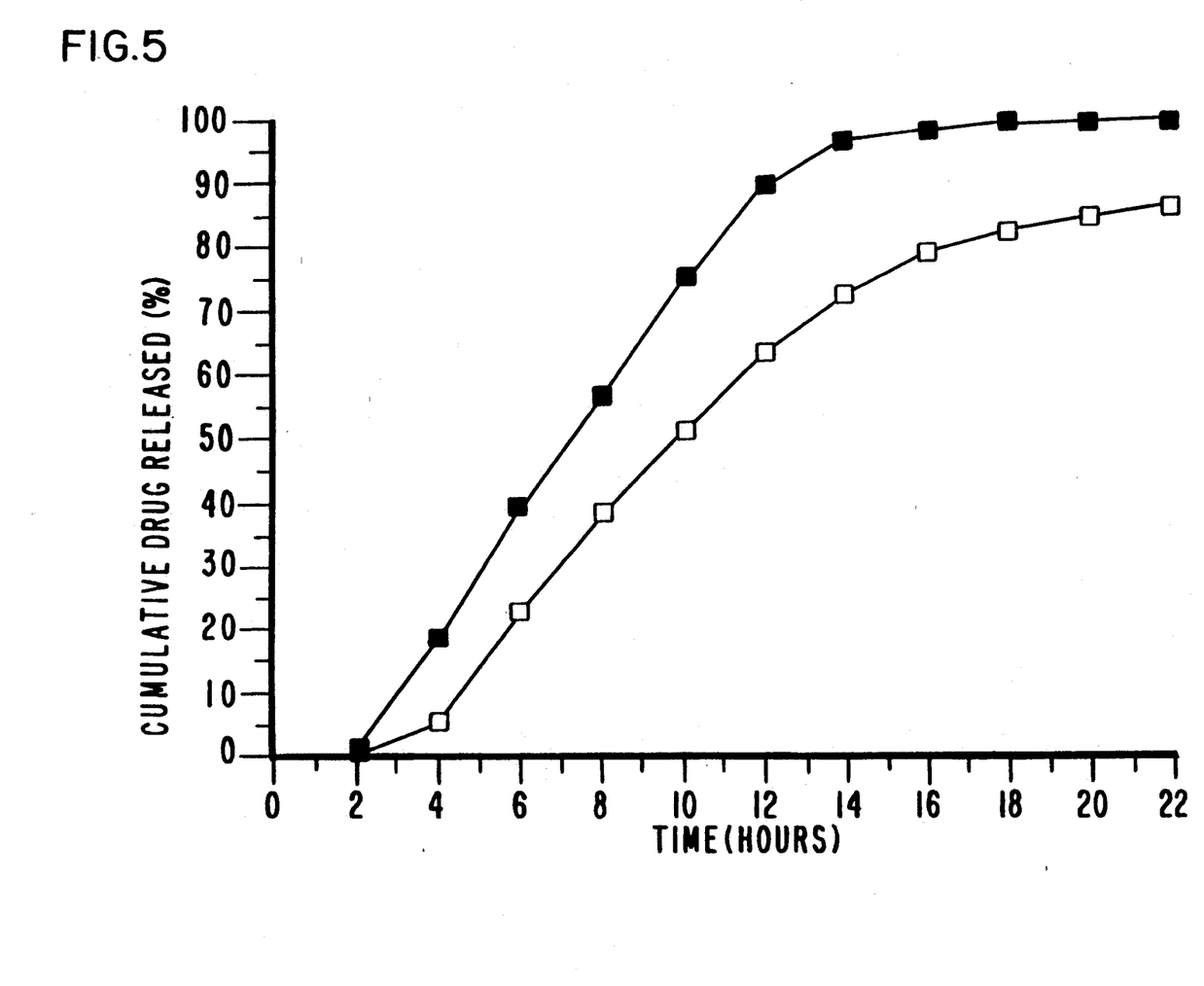
FIG. 5 depicts the release from two different dosage forms a comprising different drug layers from the dosage forms.

Two dosage forms were manufactured comprising a drug layer weighing 352 mg and a push layer weighing 174 mg. The drug layer in one manufacture comprises 50 wt % tandospirone hydrochloride, 25 wt % poly(ethylene oxide) comprising a 200,000 molecular weight, 19.95 wt % poly(ethylene oxide) comprising a 300,000 molecular weight, 4 wt % hydroxypropylmethylcellulose comprising a 11,200 molecular weight, 1 wt % magnesium stearate and 0.05 wt % of butyl hydroxytoluene. The drug layer in the other manufacture comprises 50 wt % tandospirone hydrochloride, 25 wt % poly(ethylene oxide) comprising a 200,000 molecular weight, 19.95 wt % of poly(ethylene oxide) comprising a 300,000 molecular weight, 4 wt % poly(vinyl pyrrlidone), comprising a 40,000 molecular weight, 1 wt % magnesium stearate and 0.05 wt % butyl hydroxytoluene. The push layer in both manufactures comprises 68.75 wt % poly(ethylene oxide) comprising a 7,300,000 molecular weight, 25.00 wt % sodium or potassium chloride, 5 wt % hydroxypropylmethylcellulose comprising a 17,875 molecular weight, 1.00 wt % ferric oxide and 0.25 wt % magnesium stearate. The semipermeable wall, in both manufactures, comprises 95 wt % cellulose triacetate consisting of 39.8% acetyl content and 5 wt % poly(ethylene glycol) of 3350 molecular weight. The dosage form comprises two 25 mil (0.635 mm) passageways connecting the drug layer with the exterior of the dosage form. Accompanying drawing FIG. 5 depicts the drug release over time. The dark square denotes a drug layer comprising poly(vinyl pyrrolidone) and the plain squares denote a drug layer comprising hydroxypropylmethylcellulose.

EXAMPLE 9

A dosage form is provided for delivering the succinimide drug sublingually, wherein the dosage form is sized, shaped and adapted for sublingual, that is subglossal blow or beneath the tongue for administering the drug to the hypoglossal drug receptors. The sublingual dosage form for administering tandospirone to the sublingual tandospirone receiving area to a patient in need of tandospirone therapy, comprises: (a) a wall comprising a member selected from the group consisting of cellulose acylate, cellulose diacylate, cellulose triacylate, cellulose acetate, cellulose diacetate and cellulose triacetate, which semipermeable wall surrounds; (b) an internal lumen; with (c) at least one exit passageway in the wall that connects the exterior of the sublingual dosage form with the lumen; (d) a push layer in the lumen comprising an osmotic agent, that in the presence of fluid that enters the lumen increases in volume and thereby occupies space in the lumen; and, (e) a tandospirone layer in the lumen initially separate from the push layer and in initial contact with the push layer and in initial contact with the push layer, which tandospirone layer comprises a poly(oxyethylene) comprising a $1.75 \times 10^5$ to $2.25 \times 10^5$ molecular weight and a poly(oxyethylene) comprising a $2.50 \times 10^5$ to $3.25 \times 10^5$ molecular weight, which dosage form delivers the tandospirone composition through the exit to the patient at a substantially zero order rate of release over a period of up to 24 hours to produce a tandospirone plasma level for treating depressive disorders, including major depression that is single or recurrent, bipolar disorders such as depressed depressed depressive disorders, dysthymia, major depression with or without melancholia, or cyclothymia as characterized by alternate lively and depressed moods.

EXAMPLE 10

A dosage form is provided for delivery tandospirone buccally, comprising the area adjacent to, or in the direction of the check, which dosage form is sized, shaped and adapted for positioning in the buccal area of the mouth for administering tandospirone to buccal tandospirone drug receptor areas, wherein the tandospirone buccal dosage form comprises: (a) a wall comprising a member selected from the group consisting of cellulose acylate, cellulose diacylate, cellulose triacylate, cellulose acetate, cellulose diacetate and cellulose triacetate, which buccally acceptable semipermeable wall surrounds; (b) an internal lumen; with (c) at least one exit passageway in the wall that connects the buccal exterior with the interior lumen of the buccal dosage form; (d) a push layer in the lumen comprising an osmotic agent, that in the presence of buccal fluid that enters the lumen increases in volume and thereby occupies space in the lumen; and (e) a tandospirone layer in the lumen initially separated from the push layer and in initial contact with the push layer, which tandospirone layer comprises a poly(O—CH$_2$CH$_2$)$_n$ wherein n is 4,000 to 5,500 and a second and different poly(O—CH$_2$CH$_2$)$_n$ wherein n is 6,500 to 7,400, which buccal dosage form delivers the tandospirone composition through the exit to the patient at a substantially zero order rate of drug delivery over a period up to 24 hours to produce a tandospirone plasma level for treating depressive disorders including major depression that is single or recurrent, bipolar disorders such as depressed depressed depressive disorders, dysthymia, major depression with or without melancholia, or cyclothymia as characterized by alternate lively and depressed moods.

DISCLOSURE OF USE OF THE DOSAGE FORM FOR PERFORMING A METHOD OF PRACTICING THE INVENTION

An embodiment of the invention pertains to the use of the dosage form provided by the invention in a method for delivering a drug of formula 1 at a controlled rate orally to a warm-blooded animal in need of drug formula 1 therapy, wherein the use comprises the steps of: (A) admitting into the warm-blooded animal a dosage form comprising: (1) a wall surrounding a compartment, the wall comprising a semipermeable polymeric composition permeable to the passage of fluid and substantially impermeable to the passage of drug; (2) a drug layer in the compartment comprising a formulation comprising a dosage unit amount of the drug of the formula:

for performing a therapeutic program: (3) a push layer in the compartment comprising an osmotic formulation for imbibing and absorbing fluid for expanding in size for pushing the drug of the formula from the dosage form; (4) at least one osmotic dimensioned passageway in the wall for releasing the drug; (B) imbibing fluid through the semipermeable wall at a fluid rate determined by the permeability of the semipermeable wall and the osmotic pressure across the semipermeable wall causing the push layer to expand; and (C) delivering the therapeutically active drug from the dosage form through the exit passageway to the warm-blooded animal over a prolonged period of time up to 24 hours. The drug to the formula is administer by the method of the invention for treating depressive disorders, including major depression—single or recurrent, bipolar disorder—depressed depressed depressive disorders, dysthymia, major depression with our without melancholia, or cyclothymia as characterized by alternate lively and depressed moods. The drug can be in the exo form as follows:

or, the drug can be in the endo form as follows:

or the drug can be a mixture of the exo and the endo forms.

Dosage form 10 of this invention, as seen in the above drawing figures, can be used in a method for administering a drug by the oral route, and in another method, the dosage form can be sized and shaped for administering a drug by the sublingual and buccal routes. The sublingual and buccal routes can be used for quicker therapy and they can be used when a smaller dose of drug is needed for therapy. The latter routes can be used as a by-pass of the first pass of hepatic metabolism of the drug. The drug of FIGS. (1) and (2) can be administered by the sublingual or buccal routes can be used for administering the drug for the management of anxiolytic patients. The administration of the drugs of the formulae of this invention by the sublingual and buccal routes of administration is novel and nonobvious for proving the intended therapy by these routes of administration.

In summary, it will be appreciated that the present invention contributes to the art an unobvious dosage form that possesses practical utility, can administer a drug at a dose metered release rate per unit time. While the invention has been described and pointed out in detail with reference to operative embodiments thereof, it will be understood by those skilled in the art that various changes, modifications, substitutions and omissions can be made without departing from the spirit of the invention. It is intended, therefore, that the invention embraces those equivalents within the scope of the claims which follow.

We claim:

1. A subglossal dosage form for administering tandospirone to the subglossal tandospirone receptors of a patient in need of tandospirone therapy, wherein the subglossal dosage form comprises:
   (a) a wall comprising a member selected from the group consisting of cellulose acylate, cellulose diacylate, cellulose triacylate, cellulose acetate, cellulose diacetate, and cellulose triacetate which wall surrounds;
   (b) an internal lumen;
   (c) an exit passageway in the wall that connects the subglossal environment with the internal lumen;

(d) a push composition in the lumen, comprising an osmotically fluid-activated agent that, in the presence of subglossal fluid that enters the lumen, increases in volume and thereby occupies space in the lumen; and wherein the subglossal dosage form is characterized by:

(e) a subglossal composition comprising 1 mg to 750 mg of tandospirone, a poly(oxyethylene) comprising a $1.75 \times 10^5$ to $2.25 \times 10^5$ molecular weight and a poly(oxyethylene) comprising a $2.50 \times 10^5$ to $3.25 \times 10^5$ molecular weight, which subglossal composition when administered to the patient provides tandospirone for treating depression, single and bipolar depression; depression with and without melancholia, and cyclothymia characterized by lively and depressed moods.

* * * * *